United States Patent
Choquet

(10) Patent No.: US 8,512,043 B2
(45) Date of Patent: Aug. 20, 2013

(54) BODY MOTION TRAINING AND QUALIFICATION SYSTEM AND METHOD

(75) Inventor: Claude Choquet, Montreal (CA)

(73) Assignee: 123 Certification, Inc., Montreal (CA)

( * ) Notice: Subject to any disclaimer, the term of this patent is extended or adjusted under 35 U.S.C. 154(b) by 616 days.

(21) Appl. No.: 11/663,816

(22) PCT Filed: Sep. 26, 2005

(86) PCT No.: PCT/CA2005/001460
§ 371 (c)(1),
(2), (4) Date: Mar. 27, 2007

(87) PCT Pub. No.: WO2006/034571
PCT Pub. Date: Apr. 6, 2006

(65) Prior Publication Data
US 2008/0038702 A1 Feb. 14, 2008

(30) Foreign Application Priority Data
Sep. 27, 2004 (CA) ..................................... 2482240

(51) Int. Cl.
*G09B 19/00* (2006.01)
(52) U.S. Cl.
USPC ........... 434/234; 434/219; 434/224; 434/233; 434/258; 434/260; 219/50; 219/53; 219/54; 219/602; 219/603; 219/617
(58) Field of Classification Search
USPC .................. 434/236, 247, 262, 237, 219, 224; 434/233, 234, 258, 260; 345/633; 705/1, 705/51; 219/50, 53, 54, 602, 603, 617
See application file for complete search history.

(56) References Cited

U.S. PATENT DOCUMENTS 3,867,769 A * 2/1975 Schow et al. ................. 434/234
4,124,944 A * 11/1978 Blair ............................. 434/234
(Continued)

FOREIGN PATENT DOCUMENTS

| CA | 2142416 | 9/1995 |
| CA | 2144505 | 9/1996 |

(Continued)

OTHER PUBLICATIONS

Kobayashi et al., "Simulator of Manual Metal Arc Welding with Haptic Display", ICAT 2001, Dec. 5-7, Tokyo, Japan, pp. 1-4.*

(Continued)

*Primary Examiner* — Jack Yip
(74) *Attorney, Agent, or Firm* — The Marbury Law Group PLLC

(57) ABSTRACT

The system allows training and qualification of a user performing a skill-related training exercise involving body motion in a workspace. A training environment is selected through a computer apparatus, and variables, parameters and controls of the training environment and the training exercise are adjusted. Use of an input device by the user is monitored. The 3D angles and spatial coordinates of reference points related to the input device are monitored through a detection device. A simulated 3D dynamic environment reflecting effects caused by actions performed by the user on objects is computed in real time as a function of the training environment selected. Images of the simulated 3D dynamic environment in real time are generated on a display device viewable by the user as a function of a computed organ of vision-object relation. Data indicative of the actions performed by the user and the effects of the actions are recorded and user qualification is set as a function of the recorded data.

45 Claims, 5 Drawing Sheets

(56) References Cited

U.S. PATENT DOCUMENTS

| | | | |
|---|---|---|---|
| 4,605,836 A * | 8/1986 | Retfalvi et al. | 219/130.01 |
| 4,680,014 A * | 7/1987 | Paton et al. | 434/234 |
| 4,716,273 A * | 12/1987 | Paton et al. | 219/130.1 |
| 4,867,685 A * | 9/1989 | Brush et al. | 434/234 |
| 4,931,018 A * | 6/1990 | Herbst et al. | 434/234 |
| 4,988,981 A | 1/1991 | Zimmerman et al. | |
| 5,320,538 A * | 6/1994 | Baum | 434/307 R |
| 5,554,033 A | 9/1996 | Bizzi et al. | |
| 5,708,253 A * | 1/1998 | Bloch et al. | 219/130.01 |
| 5,800,178 A * | 9/1998 | Gillio | 434/262 |
| 5,805,287 A | 9/1998 | Pettersen et al. | |
| 5,821,943 A | 10/1998 | Shashua | |
| 5,823,785 A * | 10/1998 | Matherne, Jr. | 434/234 |
| 5,846,086 A | 12/1998 | Bizzi et al. | |
| 5,882,206 A * | 3/1999 | Gillio | 434/262 |
| 5,980,256 A * | 11/1999 | Carmein | 434/55 |
| 6,062,865 A * | 5/2000 | Bailey | 434/262 |
| 6,074,213 A * | 6/2000 | Hon | 434/262 |
| 6,097,543 A * | 8/2000 | Rallison et al. | 359/633 |
| 6,104,379 A * | 8/2000 | Petrich et al. | 345/157 |
| 6,157,808 A * | 12/2000 | Hollingsworth | 434/350 |
| 6,166,744 A | 12/2000 | Jaszlics et al. | |
| 6,220,865 B1 * | 4/2001 | Macri et al. | 434/247 |
| 6,225,978 B1 | 5/2001 | McNeil | |
| 6,304,050 B1 | 10/2001 | Skaar et al. | |
| 6,396,232 B2 | 5/2002 | Haanpaa et al. | |
| 6,425,764 B1 | 7/2002 | Lamson | |
| 6,478,735 B1 | 11/2002 | Pope et al. | |
| 6,574,355 B2 | 6/2003 | Green | |
| 6,597,347 B1 | 7/2003 | Yasutake | |
| 6,697,044 B2 | 2/2004 | Shahoian et al. | |
| 6,710,298 B2 * | 3/2004 | Eriksson | 219/130.01 |
| 6,714,944 B1 | 3/2004 | Shapiro et al. | |
| 6,720,949 B1 * | 4/2004 | Pryor et al. | 345/158 |
| 6,766,036 B1 | 7/2004 | Pryor | |
| 6,863,536 B1 * | 3/2005 | Fisher et al. | 434/272 |
| 7,042,440 B2 * | 5/2006 | Pryor et al. | 345/158 |
| 7,056,123 B2 * | 6/2006 | Gregorio et al. | 434/272 |
| 7,263,491 B1 | 8/2007 | Geldermann et al. | |
| 7,404,716 B2 * | 7/2008 | Gregorio et al. | 434/272 |
| 7,500,853 B2 * | 3/2009 | Bevirt et al. | 434/262 |
| 2003/0085866 A1 * | 5/2003 | Bimber et al. | 345/156 |
| 2003/0172032 A1 * | 9/2003 | Choquet | 705/51 |
| 2004/0009459 A1 | 1/2004 | Anderson et al. | |

FOREIGN PATENT DOCUMENTS

| | | |
|---|---|---|
| CA | 2311685 | 12/2001 |
| CA | 2412109 | 6/2004 |
| FR | 2827066 | 1/2003 |

OTHER PUBLICATIONS

Hillers et al., "TEREBES: Welding Helmet with AR capabilities", Feb. 19-20, 2004, Tagungsband: International Status Conference "Virtual and Augmented Reality", pp. 1-11.*

Fast et al., "Virtual Training for Welding", 2004, Proceedings of the Third IEEE and ACM International Symposium on Mixed and Augmented Reality, pp. 1-2.*

International Search Report—PCT/CA05/001460.

International Preliminary Report on Patentability issued in PCT Application No. PCT/CA2005/001460, mailed Mar. 27, 2007.

Canadian Welding Bureau committee, "Certifying Metal Products Inspectors: Individuals with Specialized Knowledge of Various Metal Products are Targets of New Certification," Welding Canada, Apr./May 1997, p. 18. <http://proquest.umi.com/pqdweb?did=433908931&sid=48Fmt=3&clientId=19649&RQT=309&VName=PQD>.

"Benefit by Certification," Welding Canada, Jun. 1996, p. 18. <http://proquest.umi.com/pqdweb?did=433909541&sid=1&Fmt=3&clientId=19649&RQT=309&VName=PQD>.

* cited by examiner

BODY MOTION TRAINING AND QUALIFICATION SYSTEM AND METHOD

FIELD OF THE INVENTION

The present invention relates to simulators for teaching, training, qualifying and certifying purposes, and more particularly to body motion training and qualification system and method.

RELATED ART

Many skills involve a high level of dexterity from workers. For example, a surgeon must be highly manually skilled for performing operations on patients. Another skill involving a high level of dexterity and skill is welding. Minute details in a welding operation may result, for example, in a structure collapsing or not. The environment in which a welder acts is also particular as it more often involves a degree of danger, dust and darkness than not, thereby adding to the difficulty of performing a good welding operation.

A high level of dexterity or other forms of body motion may be required for athletes practicing certain sports, for human or animals practicing certain activities. For example, the body motion is crucial for divers or skiers.

Known in the art are U.S. Pat. No. 4,988,981 (Zimmerman et al.), U.S. Pat. No. 5,554,033 (Bizzi et al.), U.S. Pat. No. 5,805,287 (Pettersen et al.), U.S. Pat. No. 5,821,943 (Shashua), U.S. Pat. No. 5,846,086 (Bizzi, et al.), U.S. Pat. No. 6,166,744 (Jaszlics et al.), U.S. Pat. No. 6,225,978 (McNeil), U.S. Pat. No. 6,304,050 (Skaar et al.), U.S. Pat. No. 6,396,232 (Haanpaa et al.), U.S. Pat. No. 6,425,764 (Lamson), U.S. Pat. No. 6,478,735 (Pope et al.), U.S. Pat. No. 6,574,355 (Green), U.S. Pat. No. 6,597,347 (Yasutake), U.S. Pat. No. 6,697,044 (Shahoian et al.), U.S. Pat. No. 6,766,036 (Pryor), French patent application No. 2,827,066 (Dasse et al.)), and Canadian patent No. 2,311,685 (Choquet) and Canadian patent application No. 2,412,109 (Choquet). These patents or applications provide examples of systems, devices or methods related to virtual reality simulators. In many cases, a haptic or force feedback is provided to the user during the simulation process to achieve a more realistic effect of the conditions that a user may encounter in the simulated environment. However, such a haptic or force feedback is often unnecessary, especially when evaluating qualification of the user or for training purposes. Indeed, such a haptic or force feedback is generally used when the user has transgressed some requirements of the training process, and often involves the use of complex or expansive devices. It is like using negative reinforcement instead of positive reinforcement to help the user correct his/her skill under training. In some cases, the position of the tool used to perform the training is simulated, but the body parts of the user involved during the training are ignored, for example the position of the head of the user during the training process. Also, the working space used for performing the training is often small and impose training limits, preventing the user from being immersed in the simulation process.

Coordination of hand, head and glance is concerned in the specific field and conditions of flight simulators. But the environment and context is far different from manual dexterity or body motion, and the systems and methods have been so far impractical and expensive for body motion training and qualification. Furthermore, current manual dexterity simulators are not able to duplicate the visible world in a virtual world without compromises. For those who want manual dexterity training of a skill, a profession, a sport or reeducation, the current simulators are unsatisfactory for the rendering of the visible world at a high level. Also, current simulator systems are impractical for preproduction training of an operator who has to perform a task requiring a high level of manual dexterity due, for example, to difficult work conditions.

SUMMARY

An object of the invention is to provide a system and a method which both satisfy the need for body motion training and qualification.

Another object of the invention is to provide such a system and a method which integrate production data in real time and do not need force feedback.

Another object of the invention is to provide such a system and a method which is able to process spatial variables like a typical piece-contact distance, an angle of attack and a tilt angle having a direct effect on the activity performed, and which realistically reproduce possible defects resulting from a poor performance and enable the analysis and qualification of the defects and of the user skill.

According to one aspect of the present invention, there is provided a system for training and qualification of a user performing a skill-related training exercise involving body motion in a workspace, comprising:

an input device operable by the user in the workspace when performing the training exercise, the input device being such as to provide the user with a physical feeling of an object normally used to perform the training exercise;

a detection device positioned non-invasively with respect to the workspace, for measuring 3D angles and spatial coordinates of reference points relative to the input device and an organ of vision of the user during performance of the training exercise a display device viewable by the user during performance of the training exercise;

a computer apparatus connectable with the input device, the detection device and the display device, the computer apparatus having a memory with computer readable code embodied therein, for execution by the computer apparatus for:

selecting a training environment related to the training exercise to be performed from a training database;

adjusting variables, parameters and controls of the training environment and training exercise;

monitoring use of the input device by the user;

monitoring the 3D angles and spatial coordinates measured by the detection device and computing an organ of vision-object relation as a function thereof;

computing a simulated 3D dynamic environment in real time as a function of the training environment selected, the simulated 3D dynamic environment reflecting effects caused by actions performed by the user on objects in the simulated 3D dynamic environment as monitored from the input device and the detection device;

generating images of the simulated 3D dynamic environment in real time on the display device as a function of the organ of vision-object relation;

recording data indicative of the actions performed by the user and the effects of the actions; and setting user qualification as a function of the recorded data.

According to another aspect of the present invention, there is also provided a computer-implemented method for training and qualification of a user performing a skill-related training exercise involving body motion in a workspace, comprising:

selecting a training environment related to the training exercise to be performed from a training database;

adjusting variables, parameters and controls of the training environment and training exercise;

monitoring use of an input device providing the user with a physical feeling of an object normally used to perform the training exercise;

measuring 3D angles and spatial coordinates of reference points relative to the input device and an organ of vision of the user during performance of the training exercise;

computing an organ of vision-object relation as a function of the 3D angles and spatial coordinates;

computing a simulated 3D dynamic environment in real time as a function of the training environment selected, the simulated 3D dynamic environment reflecting effects caused by actions performed by the user on objects in the simulated 3D dynamic environment as tracked from the input device and the 3D angles and spatial coordinates;

generating images of the simulated 3D dynamic environment in real time on a display device viewable by the user during performance of the training exercise as a function of the organ of vision-object relation;

recording data indicative of the actions performed by the user and the effects of the actions; and setting user qualification as a function of the recorded data.

The system and the method have many possible uses. For example, they may be used as an helping tool for remote hiring or for remote annual wage evaluation. They may also be used for performing accessibility tests prior to practicing the real work, or to bid certain works according to code requirements, or for preproduction training, or remote monitoring during working of an operator. In the bid case or remote hiring, plants will have the possibility of cloning a scaled-down engineering division. For consulting firms winning a turn key contract for plant construction abroad, they will have the possibility to hire local workers while making sure that they are apt to skillfully perform the work. The system and the method are particularly usable in the field of welding, although they are not limited to this field.

BRIEF DESCRIPTION OF THE DRAWINGS

A detailed description of preferred embodiments will be given herein below with reference to the following drawings, in which like numbers refer to like elements.

DETAILED DESCRIPTION OF THE PREFERRED EMBODIMENTS

The skills related to welding have been chosen in this disclosure to describe embodiments of the invention for illustrative purposes only. It should be understood that any other skill involving a degree of manual dexterity or other kind of body motion and a qualification thereof is contemplated.

As used in connection with this disclosure, the expression "monitoring" refers to an action consisting of measuring, checking, watching, recording, keeping track of, regulating or controlling, on a regular or ongoing basis, with a view of collecting information.

Many occupations, professions, works, crafts, trades, sports, activities possibly with sensitive reaction, etc. require minimal qualifications to operate a tool, a machine, etc., i.e. certain skills involving a manual or body motion activity. A common point of these skills resides in spatial location tracking of body and/or object to obtain information which may be called spatial essential variables (S.E.V.). These S.E.V. are specific to each activity. Their numbers vary and their inter-relationships may be more or less complex. A simulator system for inserting a nail with a hammer will not have the same future as a simulator system for cutting a diamond, for performing a surgical operation or even for welding, or brazing, or cutting various types of meat properly. Welding involves more than forty (40) essential variables (E.V.). There are even standards attempting to define nomenclature related to the E.V. in this field to avoid confusion on the meaning of these E.V. A worker such as a carpenter must also have a manual dexterity as a function of the laws of physics (kinematics, dynamics) for example for hammering in a nail at a good depth. A welder, for his/her part, has to face the following current allusion in the world of welding: "a nice weld may be poor and an inelegant weld may be good". This expression is based on the fact that the welder has no access to the final microscopic results showing the regeneration of the grains or the root fusion ensuring welding integrity. Likewise, a surgeon has no access to the final results at the cellular level ensuring cellular regeneration. Each of these activities commonly involves manual dexterity or neuromuscular variables in addition to a neurocerebral knowledge. All the activities requiring psychomotor knowledge also require a capacity for 3D recognition of space location.

The combination of the 3D location angle and XYZ coordinate data are reference points required for positioning purposes. The kinematics of these reference points enables to find trajectories, speeds and accelerations of points in space and to associate them to masses which can then be used in the processing of the manual dexterity.

Figure 1:
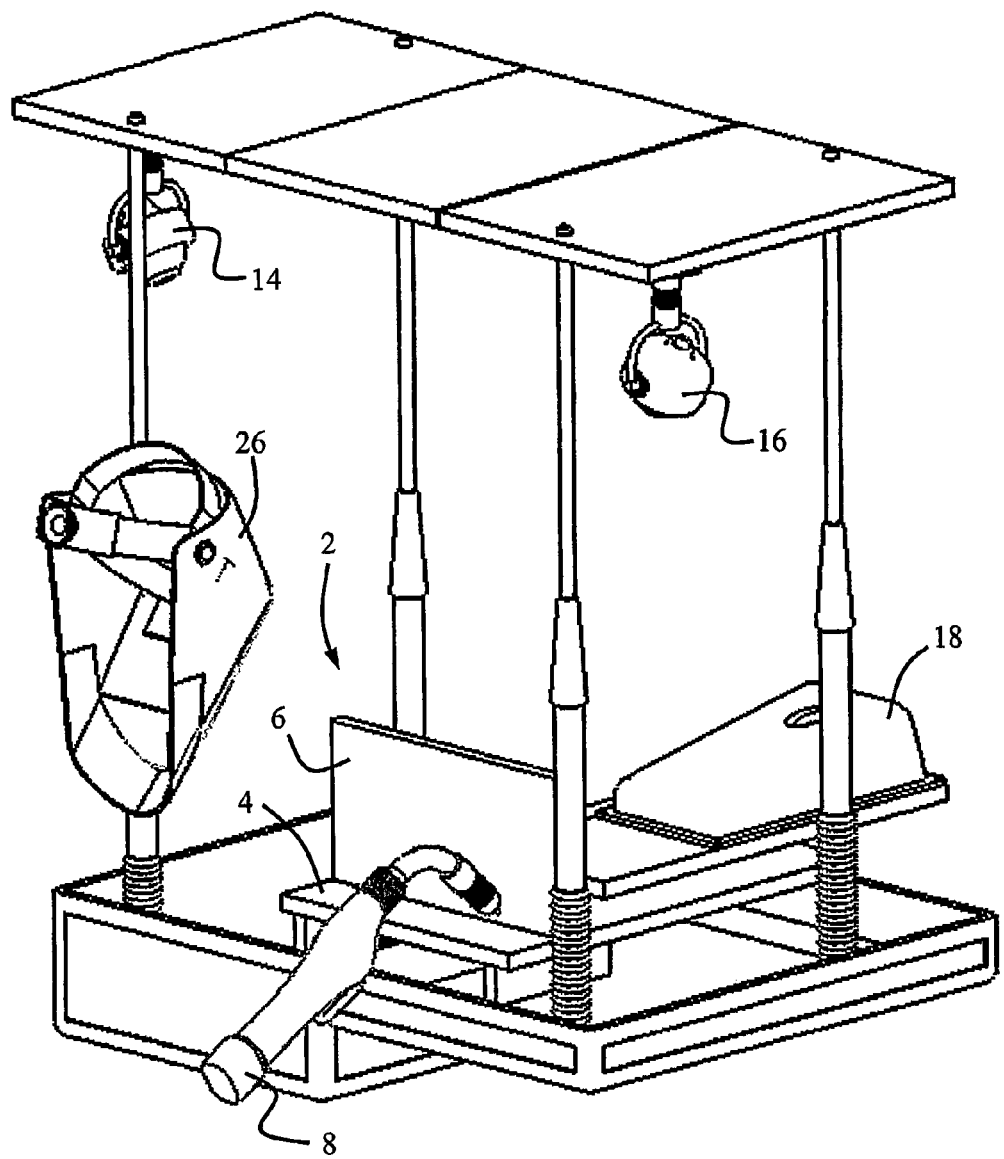
FIG. 1 is a perspective view of a training station and workspace of the disclosed system for training and qualification.
Figure 3:
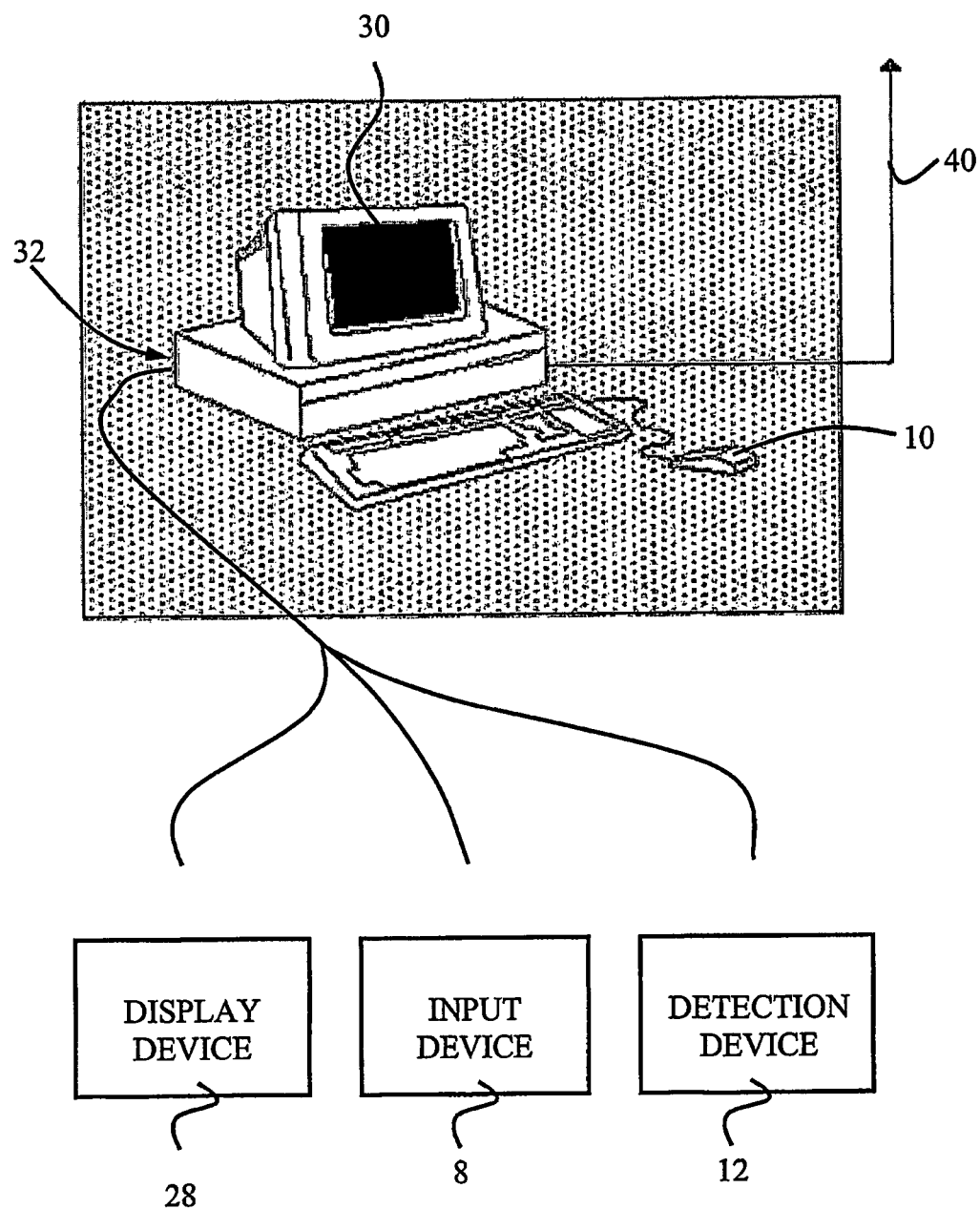
FIG. 3 is a schematic diagram of a computer station of the disclosed system.

Referring to FIGS. 1 and 3, there is shown a system for training and qualification of a user performing a skill-related training exercise involving bogy motion in a workspace 2. As used in connection with this disclosure, the expression "workspace" represents a space in which a training exercise is performed. The space may be arranged as a scene or a setup with physical objects related to the training exercise if desired. In the illustrated case, the training exercise relates to the field of welding and consists in welding two pieces 4, 6 together, the pieces 4, 6 being positioned in the space as if a real welding operation were to be achieved. Thus, the workspace may comprise physical objects subjected to the actions performed by the user during the training exercise.

The system comprises an input device 8 operable by the user in the workspace 2 when performing the training exercise. The input device 8 is such as to provide the user with a physical feeling of an object normally used to perform the training exercise. It may be made of a physical object imitating a tool normally used to perform the training exercise. In the illustrated case, the input device is made of a dummy welding torch. The input device may take the form of any suitable accessory to the training exercise to carry out. For example, it may be a pen to practice writing skills, a scalpel to practice surgery skills, a tool to practice workmanship, etc. It may be simply a computer mouse 10. It may also be a sensor glove or suit translating body motion by the user to commands for manipulating objects in a virtual environment.

A detection device 12 is positioned non-invasively with respect to the workspace 2, for measuring 3D angles and spatial coordinates of reference points relative to the input device 8 and an organ of vision of the user during performance of the training exercise. As used in connection with this disclosure, the expression "non-invasively" refers to detection techniques whereby the detection device does not interfere with the body motion and the vision of the user during the training exercise. The detection device may be positioned within, outside or partially within the workspace 2, as long as it does not interfere with the body motion and the vision of the user. As used in connection with this disclosure, the expression "organ of vision" represents something that is used to see objects in the workspace 2, and which defines a viewpoint. It may be but is not limited to the eyes of a user, his/her head, a display device or other accessory such as a helmet 26 through which or by which a user may see the objects in the workspace 2. In the case where a sensor glove or suit is used, sensors in the glove or suit may form parts of the detection device 12. In the illustrated case, the detection device 12 comprises a pair of electronic sensors 14, 16 on sides of the workspace 2 and an other electronic sensor 18 positioned on a side of the workspace 2 opposite to the user.

Figure 4:
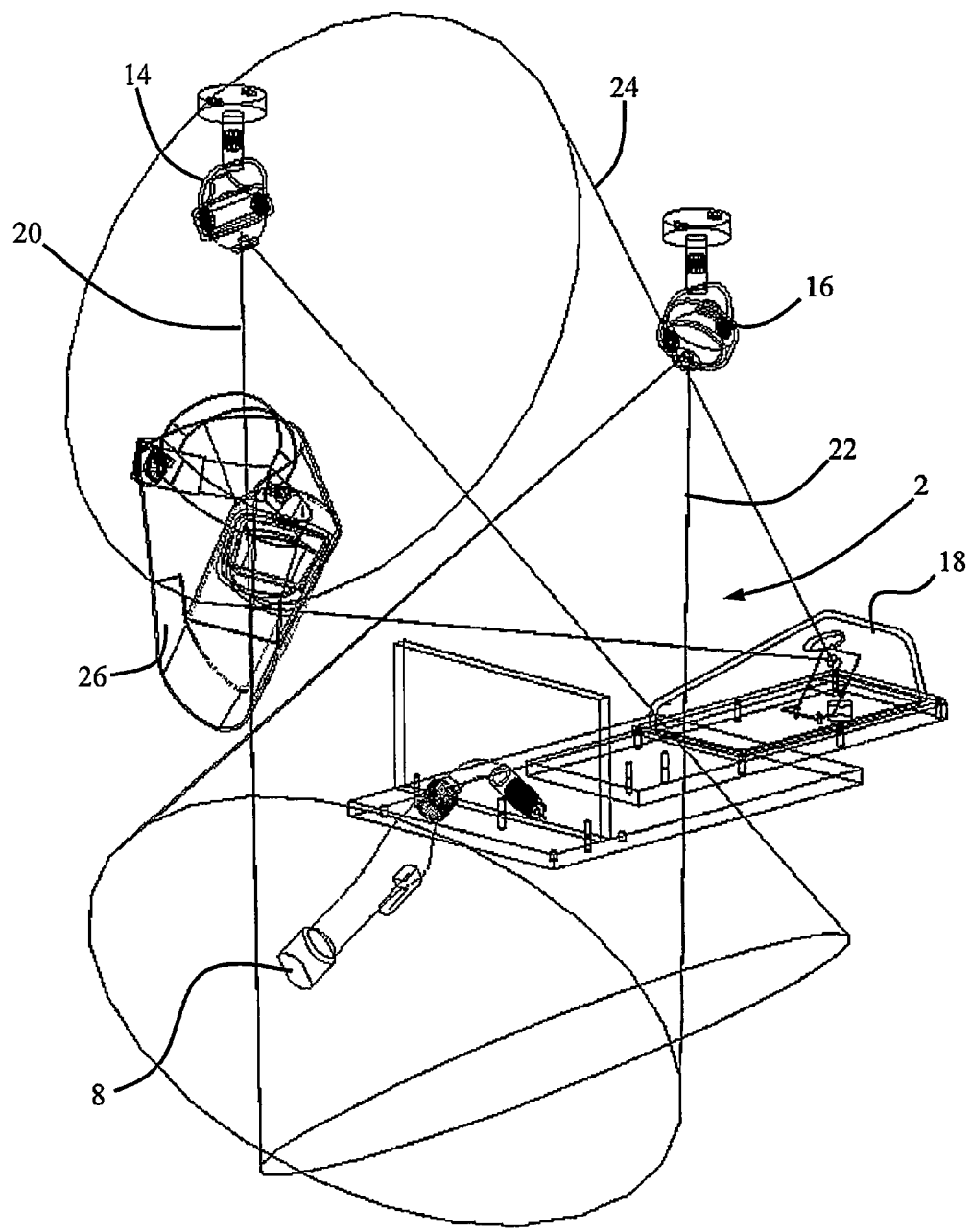
FIG. 4 is a schematic diagram of a detection device of a training station of the disclosed system.

Referring to FIG. 4, the electronic sensors 14, 16 are directed to at least cover portions of the workspace 2 where the user may be led to move the input device 8 during the training exercise, in order to be capable of continuously tracking the input device 8 during the training exercise. The electronic sensor 18 is arranged to at least cover a portion of the workspace 2 where the organ of vision 26 of the user may be moved during the training exercise, in order to be capable of continuously tracking the organ of vision 26 during the training exercise. Cones 20, 22 depict the fields of view of the electronic sensors 14, 16 while cone 24 depicts the field of view of the electronic sensor 18. Reflectors positioned on the input device 8 may be used in combination with the electronic sensors 14, 16 thereby forming emitter-receptor arrangements, to facilitate the angle and location tracking of reference points relative to the input device 8. Likewise, reflectors positioned near the organ of vision of the user, for example on the helmet 26, may be used in combination with the electronic sensor 18, thereby also forming emitter-receptor arrangements, to facilitate tracking of reference points relative to the organ of vision and determination of the viewpoint of the user. The electronic sensors 14, 16 may for example be formed of video cameras while the electronic sensor 18 may be formed of an infrared detector. Other non-invasive detection technologies may be used and combined together if desired, for example video, ultrasound, MEMS (Micro Electro-Mechanical System), etc. The detection device 12 preferably remains operational at all time during performance of the training exercise, for tracking purposes. The detection device 12 may measure or otherwise track the input device 8 and the organ of vision 26 at a regular interval or continuously, depending on the needs. The positioning of the detection device may be adapted to the kind of training exercise to be performed by the user. For example, the electronic sensors 14, 16, 18 may be positioned at locations different from those illustrated in FIGS. 1 and 4, as long as they fulfil their function as hereinabove explained. Depending on the kind of sensor, only one sensor may be used to track the input device 8 if desired.

Figure 2:
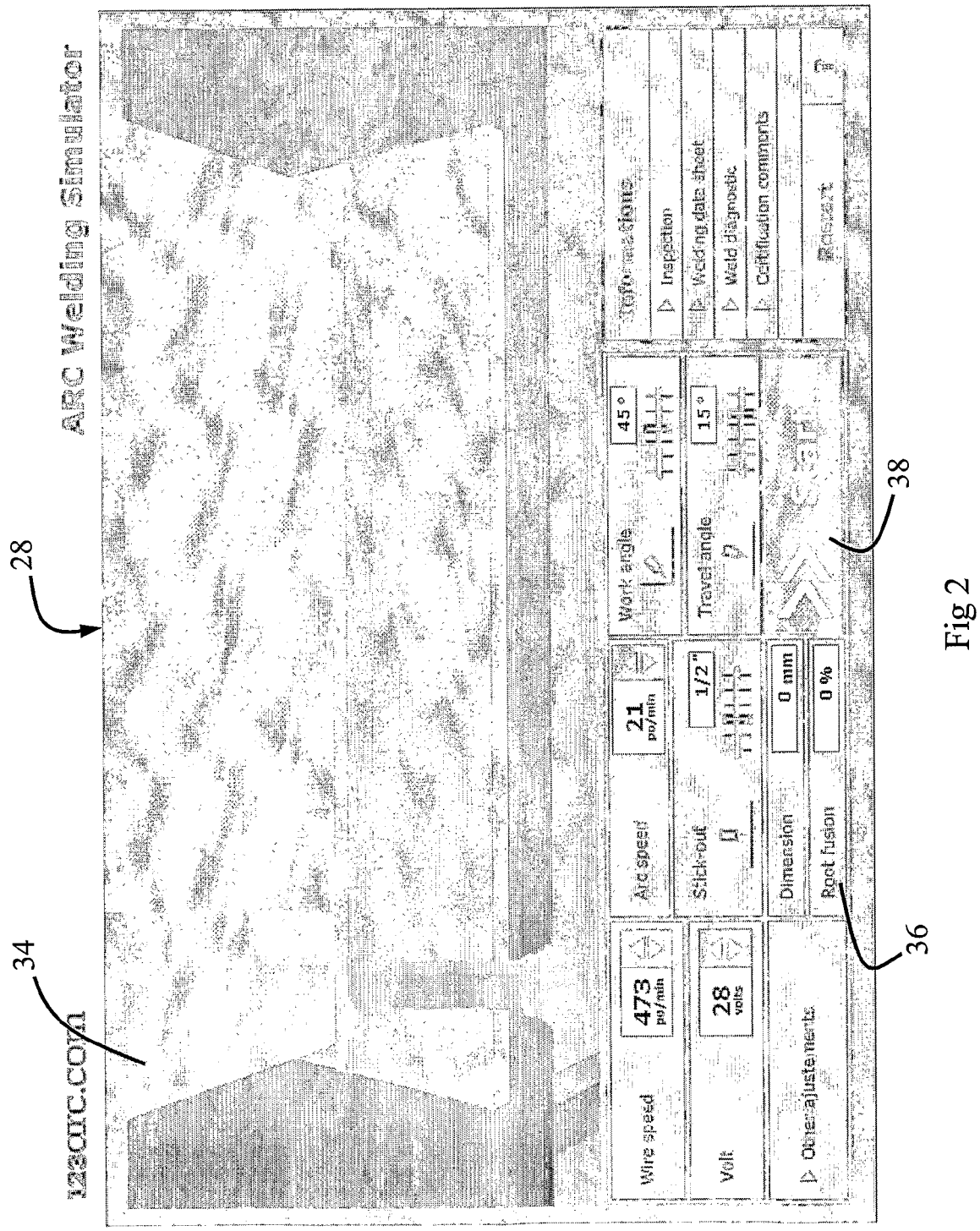
FIG. 2 is a schematic diagram illustrating an image on a display device of the disclosed system.

Referring to FIGS. 1 and 3 again, a display device 28 viewable by the user during performance of the training exercise is provided. The display device may be integrated in a pair of goggles, the helmet 26 as in the illustrated case, or any other suitable structure wearable by the user during the training exercise to be viewable at all time during performance of the training exercise. Depending on the training exercise to be performed by the user, the display device 28 may be provided by a computer monitor 30. In the case where it is integrated in the helmet 26 or a pair of gaggle, the display device 28 may have a degree of transparency letting the user see the workspace 2. FIG. 2 illustrates an example of images generated on the display device 28.

A computer apparatus 32 connectable with the input device 8, the detection device 12 and the display device 28, is provided. The computer apparatus 32 has a memory with computer readable code embodied therein, for execution by the computer apparatus 32 for selecting a training environment related to the training exercise to be performed from a training database. The computer apparatus 32 also adjusts variables, parameters and controls of the training environment and training exercise. The adjustments may be carried out automatically or manually, depending on the needs of the training exercise. The computer apparatus 32 monitors use of the input device 8 by the user, monitors the 3D angles and spatial coordinates measured by the detection device and computes an organ of vision-object relation as a function of the 3D angles and spatial coordinates so measured. The computer apparatus 32 further computes a simulated 3D dynamic environment in real time as a function of the training environment selected, so that the simulated 3D dynamic environment reflects effects caused by actions performed by the user on objects in the simulated 3D dynamic environment as monitored from the input device 8 and the detection device 12. The computer apparatus 32 generates images of the simulated 3D dynamic environment in real time on the display device 12 as a function of the organ of vision-object relation, records data indicative of the actions performed by the user and the effects of the actions, and sets user qualification as a function of the recorded data. The recording of the data may be used for providing a replay mode for the user so that he/she or a teacher or a third party may see what the user has done during the training exercise.

The simulated 3D dynamic environment may involve a more realistic virtual representation of the tool than the physical object used as the input device 8. The input device 8 may have a stopwatch circuit measuring elapsed time during the training exercise and providing time data to the computer apparatus 32 for timing functions of the training exercise. The input device 8 may be provided with a haptic interface responsive to a collision condition detected by the computer apparatus 32 during the training exercise while computing the simulated 3D dynamic environment, to relay a sense of physical sensation to the user as a function of the collision condition.

Referring to FIG. 2, there is shown an example of images generated on the display device 28 during performance of a training exercise. The images may be mathematically generated by the computer apparatus 32. A visual indicator 34, for example a red dot appearing in the images on the display device 28, or a sound indicator responsive to a collision condition detected by the computer apparatus during the training exercise while computing the simulated 3D dynamic environment may be also provided to relay the collision condition to the user. The images an the display device 28 may be formed of virtual images superimposed over other virtual images as modelled from the computing of the simulated 3D dynamic environment. The display device 28 may provide informative data 36 superimposed over the images as modelled from the computing of the simulated 3D dynamic environment.

The training exercise may be initiated by a user action on the input device 8 or the computer apparatus 32, for example by pressing a start button 38.

Depending on the kind of training environment, the computing of the simulated 3D dynamic environment may involve virtual modelling of phenomena resulting from the effects, and representation of the phenomena in the images generated on the display device. The phenomena may be, for example, changes of states and properties of matter at interfaces and in portions of objects in the simulated 3D dynamic environment. The phenomena may also be possible defects resulting from a poor performance of the user during the training exercise. The computing of the simulated 3D dynamic environment may involve determining essential variables typical to a skill associated with the training exercise. The essential variables may be trajectory, speed and skill activity angle of objects interacted with during the training exercise. The computing of the simulated 3D dynamic environment may then involve linking the 3D angles and spatial coordinates of the reference points to the essential variables. The variables, parameters and controls may involve a tolerance degree for qualification of the training exercise. The user qualification may be set by pixel analysis of the data recorded. The computing of the simulated 3D dynamic environment may also involve replicating the physical objects in the simulated 3D dynamic environment.

The data used for computing the simulated 3D dynamic environment may consist of data related to a code of conduct, a code of practice, physics law equations, technical standards and specifications for physical activities requiring a training, a qualification and possibly a certification, and training scenarios and environments, for example elements of tests, parameters and basic controls. The disclosed system may be combined with the system disclosed in Canadian patent No. 2,311,685 (Choquet) for third party certification purposes, and with the system disclosed in Canadian patent application No. 2,412,109 (Choquet) for distributed environment simulation purposes, the disclosures of which are incorporated herein by reference. The computer apparatus 32 may thus be provided with a communication link 40 for communication with other network components via a communication network.

The physics law equations may be used to create, to deposit or fill or to create matter defects, and to move a virtual matter in space. Virtual matter may for example be molten metal, painting, ink or lead, as would be deposited with tools like a welding gun, a brazing gun, a painting gun, a pencil. The virtual matter may for example be animal or human virtual skin and muscles, meat, vegetal, or metal to be cut. The object used to perform the training exercise may be a real or original or dummy physical object like a pencil, a welding handle, a brazing handle, a lancet/scalpel, a chisel etc., or simply a mass such as a glove which reproduces weight and inertia. It may also be reproduced virtually, for example a hairdresser chisel.

The organ of vision-object relation allows to deposit/move/position virtual matter with a translation motion from a point A to a point B located anywhere in space. Thus a translation training exercise may be taught as a function of a motion straightness tolerance. The organ of vision-object relation also allows processing of time-related data as provided by the stopwatch, for example an amount of matter deposited. A training exercise may thus be taught as a function of acceleration and speed range tolerances.

The display device 28 allow seeing the work carried out in real time while making it possible to give properties to the matter (solid, liquid and gas) and to associate an output after processing with the stopwatch. For example, a virtual digital thermography temperature may be displayed on the display device 28 to show heat intensities with color arrangements to thereby simulate temperature according to time. The measurement unit of the virtual matter may be a pixel. The pixels may be studied to show, simulate, qualify and certify the manual dexterity of the user.

The disclosed system includes the capture of three-dimensional data and then allocates properties to material and also provide visual and sound feed-back if required. There are different types of transmitting surfaces and their selection depends on the signals to be used, for example ultrasound, infrared, digital or video imagery, etc., which at their turn are selected based on practical and cost considerations and design choices. Colors, shapes and motions in the images may be used to detect objects. The objects in the workspace 2 may be real or virtual. In the illustrated example, the objects which are to be welded are made of a real assembly of 2 aluminum plates normalized according to CSA W47.2 standard. A tool such as the welding gun 8 may be real or virtual, in which case a ballasted glove may be used to collect three-dimensional data related to the body motion of the user. An activation/deactivation function of the stopwatch may be provided on the tool. In the illustrated example, the tool is in the form of a handle for usual production welding in which the activation/deactivation function (trigger) is connected to the computer-implemented process. The handle may be provided with emitting, transmitting or reflecting surfaces depending on the type of detection device 12 used.

Determination of the spatial location of the tool 8 may be achieved by means of a lookup table method, a triangulation method or any other methods allowing determination of the spatial location of the tool 8. Preferably, the method will allow a six degrees of freedom detection for spatial location determination.

The lookup table method consists in detecting a space location by a matrix tracking process, for example by using two matrix devices positioned to cover two different planes to capture the 3D location of the scene in the workspace 2. In this case, the tool 8 may be provided with two emitters, transmitters or reflectors, depending on whether the matrix devices are active or passive and their configuration, to provide position data processed by the computer apparatus 32 to transpose the tool 8 in the virtual environment, for example applying trigonometry rules.

The triangulation method allows detecting the tool 8 in the workspace 2 with only one detection device. In this case, the tool may be provided with three emitters, transmitters or reflectors positioned triangularly. When the detection device detects the emitters, transmitters or reflectors, it produces X, Y, Z position data and angle data (for example pitch, roll and yaw).

The methods may be used alone or combined together or with other tracking methods. The choice may depend on the access limitations of the workspace 2 and the kind of training exercise to be performed, while seeking optimization for the user visual feedback. In the field of welding, the training tool may be bulky and heavy while in another field like surgery, the training tool maybe small and light. Thus, the type of detection devices and the tracking methods will likely be different from case to case, in addition to economic and efficiency issues.

During the training exercise, the emitters, transmitters or reflectors on the tool handle 8 are detected by the receivers who transmit position data to the computer apparatus for processing. The real coordinates of the emitters, transmitters or reflectors may be computed in real time when the receivers detect them simultaneously.

Once the real positions of the emitters, transmitters or reflectors are known, each displacement of the handle 8 may be reported in real time in a simulator, such as an ARC® simulator. The detected positions allow computing three-dimensional information (for example, the final length of an electric arc, the work angle and drag angle) in the computer process implementing an algorithm. Once the computer process is completed, the resulting information may be subjected to a certification process as disclosed in Canadian patent No. 2,412,109 (Choquet). It will then be possible to combine the processed information (for example, the 3D image capture, the image reconstruction for vision feedback, tactile and sound feedback for educational considerations) with those who were collected by the system of the aforesaid patent to obtain all the relevant information for achieving a standard welding operation by means of virtual certification now available via a communication network, such as internet.

Figure 5:
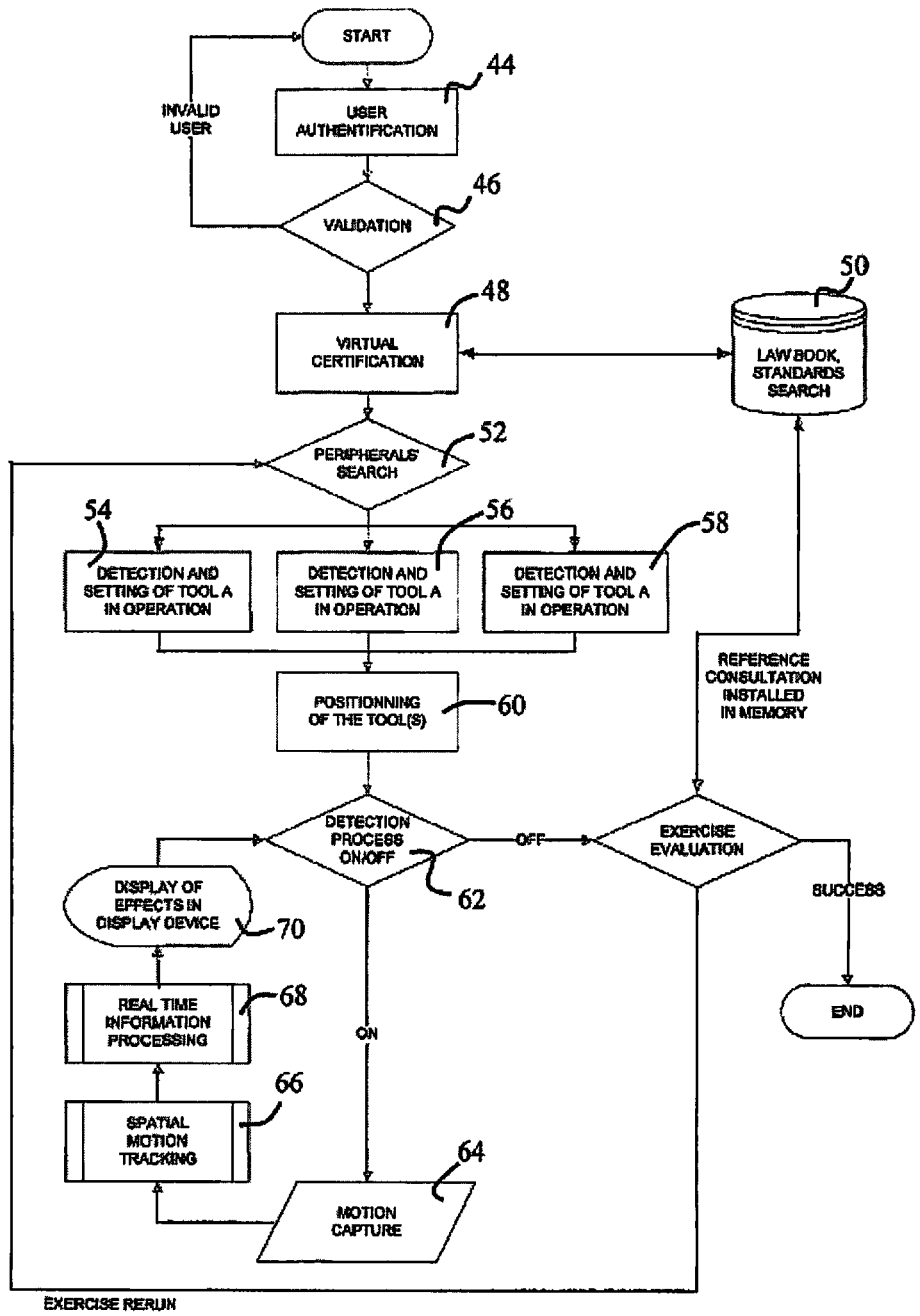
FIG. 5 is a flowchart illustrating a possible procedure implemented by the disclosed system.

Referring to FIG. 5, there is shown a flowchart illustrating a possible procedure implemented by the disclosed system in the case where the training exercise consists in performing a welding operation.

The first step as depicted by block 44 may consists of a user authentication followed by validation of the user as depicted by block 46. The user authentication may be achieved in various manner, for example through a web cam for visual proof, or a personal identification number and password assigned to the user.

As depicted by block 48, a virtual certification process may be initiated if desired, once the user has been validated by the system. The virtual certification process refers to a database 50 to search for law book and standards to be used for the training exercise. The training exercise may be selected as a function of these standards and the variables, parameters and controls of the training environment may be adjusted if needed or if desired.

A search of the peripherals connected to the computer apparatus may be achieved, as depicted by block 52. This step may set the electronic receivers forming the detection device into operation to measure the position information according to the case required for the application. It may also set the display device in operation to display the virtual environment and the relevant information regarding the training exercises to the user. Possible sound equipment may also be set in operation, while detection and setting of the tools used by the user in operation may also be achieved as depicted by block 54, 56 and 58.

The user is now ready to perform the training exercise. As depicted by block 60, the user may position the object, for example the tool 8 provided with the spatial tracking elements of the detection device 12, as needed. The computer apparatus 32 begins creation of the scene activity and, if necessary, starts the stopwatch and the processing algorithm in response, for example, to an action of a finger on a trigger or an action triggered by a combination of signals from the detection device 12 and the computer application, as depicted by block 62. Other triggering events or conditions may be implemented, for example a condition where an electric circuit is closed or opened by appropriate displacement of the tool 8 by the user. Such a triggering condition may be obtained in the case where the tool 8 forms a welding electrode, by bringing the electrode closer at an arc striking distance from the object to be welded, causing formation of an arc. Then, the user must find and preserve the appropriate distance to avoid arc extinction as in GMAW (Gas Metal Arc Welding). A different triggering action by striking the electrode against the object may be required as in SMAW (Shielded Metal Arc Welding).

The information (motion) to be processed with respect to the reference material, for example the tool 8, is captured by the computer apparatus 32 from the detection device 12, as depicted by block 64. As hereinabove indicated, a glove provided with virtual or real functions, like a real tool, may be used as the tool 8.

As depicted by block 66, the visual and sound data are processed by the computer apparatus 32 to compute the 3D space location of the reference points with respect to the material used as spatial tracking elements of the detection device for the object/tool 8. Likewise, the 3D space location of the reference points with respect to the user viewpoint are computed using the data, and the organ of vision-object relation is also computed.

As depicted by block 68, a position of the reference points in the 3D space is determined by simultaneous processing of the signals produced by the detection device 12, while the material moves tridimensionally, kinematically and dynamically. In the example case of a welding operation, a hot spot is thermodynamically created virtually in the space or environment. The materials to be joined are assembled with a welding bead produced by translation of this hot spot feeded virtually with metallurgical essential variables enabling fusion.

The work angle, travel angle and the final length data are determined in real time by processing the data captured by the detection device 12, with the reference points. These E.V. are manageable with the capture of the position in space and its relative location with respect to the viewpoint.

As depicted by block 70, the images are generated on the display device 28, so that the user may look at the creation of the bead deposit and correct in real time the final length or the tool angles to thus obtain a welding in conformity with the standards in force. At the same time, when the hand provided with the mass of the tool 8 moves in the real space, the images on the display device 28 reflect a welding bead having all the features of a real welding.

A sound feedback loop may be also achieved during the exercise to guide the user for performing a proper transfer mode and for user recognition purposes.

Once the training exercise is finished and the detection is stopped, as again depicted by block 62, the exercise is evaluated by processing the data created and recorded during performance of the exercise. The data may be created as per the certification algorithm as disclosed in Canadian patent application No. 2,311,685 (Choquet) in conformity with a standard identified at the time of the user authentication. The processed data may be validated with the database 50 and with the mathematical equations used to process the size of the bead, its root penetration and the acceptable or unacceptable physical state according to acceptance criteria based on a code of conduct or rule of the art.

The computer-implemented process may be distributed across network components in communication with the computer apparatus 32.

The data structures and code used by the computer apparatus 32 are typically stored on a computer readable storage medium or memory, which may be any device or medium that can store code and/or data for use by a computer system. This includes, but is not limited to, magnetic and optical storage devices such as disk drives, magnetic tape, CDs (compact discs) and DVDs (digital video discs), and computer instruction signals embodied in a transmission medium (with or without a carrier wave upon which the signals are modulated). For example, the transmission medium may include a communications network, such as the internet. The computer apparatus 32 may be a local or a remote computer such as a server and include any type of computer system, including, but not limited to, a computer system based on a microprocessor, a mainframe computer, a digital signal processor, a personal organizer, a device controller, and a computational engine within an appliance.

The computer implemented process may be embodied in a computer program product comprising a memory having computer readable code embodied therein, for execution by a processor. On a practical level, the computer program product may be embodied in software enabling a computer system to perform the operations, described above in detail, supplied on any one of a variety of media. An implementation of the approach and operations of the invention may be statements written in a programming language. Such programming language statements, when executed by a computer, cause the computer to act in accordance with the particular content of the statements. Furthermore, the software that enables a computer system to act in accordance with the invention may be provided in any number of forms including, but not limited to, original source code, assembly code, object code, machine language, compressed or encrypted versions of the foregoing, and any and all equivalents.

The disclosed system may comprise multiple input devices operable by a same user or different users, and may track two or more hands as well as objects manipulated by these hands. The sound, visual or contact feedback may be implemented together or individually in production situations. The visual feedback provided to the user during performance of the training exercise is instantaneous. It allows production monitoring, and allow the user to understand that this equipment is not for spying him/her but is a companion during phases of difficult access or for other reasons. The sound feedback may be generated from pre-recorded sounds associated with electric arc transfer modes or any other effects related to the training exercise and environment. For example, the key sound of a bee is typical of an axial spray mode, globular frying and short-circuit cracking. The contact feedback may be used to show that when a welder touch the virtual plate, an undercut is created, which is a normal defect as soon as there has been a contact with the plate. With the disclosed system, a welder may be provided with a helmet having an LCD display showing real time data while the welder produces real metal in fusion as the welder welds. In addition, a virtual image of the metal in fusion could be superimposed over the real image in the field of vision of the welder to thereby provide the welder with required information to achieve a standard-complying and earth friendly welding as with this equipment, the welder will pollute less the environment as he/she will achieve clean welding. Thus, the disclosed system may be used to train while integrating real time production data. The use in production of the various visual, contact and sound feedbacks together or individually for monitoring purposes is possible as the user performs the exercise. Thus, the qualification is in real time. For example, a welder knows that by keeping his/her speed, trajectory, angle and distance in conformity and that the electric element is also in conformity, then the welding operation is in conformity with the standard. At the level of the sound feedback, it is possible to incorporate a sound to a real welding machine to confirm that the operation is in conformity. At the level of the visual feedback, the speed, trajectory, angle and distance data may be provided on the display device 28 at all time. The disclosed system may be used for remotely controlled production namely e-production or teleproduction purposes.

In the disclosed system, the body motion in a 3D scene environment can be as complete as in reality. The disclosed system may also be used for training in nano-environments with nano-tools, for example for nano-forging and micro-joining applications.

While embodiments of this invention have been illustrated in the accompanying drawings and described above, it will be evident to those skilled in the art that changes and modifications may be made therein without departing from the essence of this invention.

The invention claimed is:

1. A system for training and qualification of a user performing a skill-related training exercise involving body motion in a workspace, comprising:
an input device operable by the user in the workspace when performing the training exercise, the input device being such as to provide the user with a physical feeling of an object normally used to perform the training exercise on a real or virtual assembly, wherein the input device is a real or dummy welding torch;
a detection device positioned non-invasively with respect to the workspace, for measuring 3D angles and spatial coordinates of reference points relative to the input device and an organ of vision of the user during performance of the training exercise, wherein the detection device comprises at least two sensors having conical fields of view, at least one sensor configured to measure the 3D angles and spatial coordinates of reference points relative to the input device and at least one sensor configured to measure the 3D angles and spatial coordinates of reference points relative the organ of vision of the user;
a display device viewable by the user during performance of the training exercise;
a computer apparatus connectable with the input device, the detection device and the display device, the computer apparatus having a non-transitory computer readable medium with computer readable code embodied therein, for execution by the computer apparatus for:
selecting a training environment related to the training exercise to be performed from a training database;
adjusting variables, parameters and controls of the training environment and training exercise;
monitoring use of the input device by the user;
monitoring the 3D angles and spatial coordinates measured by the detection device and computing an organ of vision-object relation as a function thereof;
computing a simulated 3D dynamic environment in real time as a function of the training environment selected, the simulated 3D dynamic environment reflecting effects caused by actions performed by the user on objects in the simulated 3D dynamic environment as monitored from the input device and the detection device;
generating images of the simulated 3D dynamic environment in real time on the display device as a function of the organ of vision-object relation;
recording data indicative of the actions performed by the user and the effects of the actions; and
setting user qualification as a function of the recorded data, wherein setting user qualification comprises comparing the recorded data to a welding standard or code and granting certification if the recorded data meets or exceeds the acceptance criteria of the welding standard or code.

2. The system according to claim 1, wherein the input device comprises a physical object imitating a tool normally used to perform the training exercise.

3. The system according to claim 2, wherein the simulated 3D dynamic environment comprises a more realistic virtual representation of the tool than the physical object used as the input device.

4. The system according to claim 1, wherein the input device comprises stopwatch circuit measuring elapsed time during the training exercise and providing time data to the computer apparatus for timing functions of the training exercise.

5. The system according to claim 1, wherein the input device comprises a haptic interface responsive to a collision condition detected by the computer apparatus during the training exercise while computing the simulated 3D dynamic environment, the haptic interface relaying a sense of physical sensation to the user as a function of the collision condition.

6. The system according to claim 1, further comprising at least one of a visual indicator and a sound indicator responsive to a collision condition detected by the computer apparatus during the training exercise while computing the simulated 3D dynamic environment and relaying the collision condition to the user.

7. The system according to claim 6, wherein the images on the display device comprise the visual indicator.

8. The system according to claim 1, wherein the detection device is operational at all time during performance of the training exercise.

9. The system according to claim 1, wherein the detection device comprises emitter-receptor arrangements positioned on the input device and on sides of the workspace, and emitter-receptor arrangements positioned on a side of the workspace opposite to the user and near the organ of vision of the user.

10. The system according to claim 1, wherein the display device is integrated in one of a pair of goggles, a helmet and a structure wearable by the user during the training exercise to be viewable at all time during performance of the training exercise.

11. The system according to claim 1, wherein the images on the display device comprise virtual images superimposed over other virtual images as modelled from the computing of the simulated 3D dynamic environment.

12. The system according to claim 1, wherein the display device has a degree of transparency letting the user see the workspace.

13. The system according to claim 1, wherein the display device comprises informative data superimposed over the images as modelled from the computing of the simulated 3D dynamic environment.

14. The system according to claim 1, wherein the training exercise is initiated by a user action on one of the input device and the computer apparatus.

15. The system according to claim 1, wherein the computing of the simulated 3D dynamic environment comprises virtual modelling of phenomena resulting from the effects, and representation of the phenomena in the images generated on the display device.

16. The system according to claim 15, wherein the phenomena comprise changes of states and properties of matter at interfaces and in portions of objects in the simulated 3D dynamic environment.

17. The system according to claim 15, wherein the phenomena comprise possible defects resulting from a poor performance of the user during the training exercise.

18. The system according to claim 1, wherein the computing of the simulated 3D dynamic environment comprises determining essential variables typical to a skill associated with the training exercise.

19. The system according to claim 18, wherein the essential variables comprise trajectory, speed and skill activity angle of objects interacted with during the training exercise.

20. The system according to claim 18, wherein the computing of the simulated 3D dynamic environment comprises linking the 3D angles and spatial coordinates of the reference points to the essential variables.

21. The system according to claim 1, wherein the variables, parameters and controls comprise a tolerance degree for qualification of the training exercise.

22. The system according to claim 1, wherein the user qualification is set by pixel analysis of the data recorded.

23. The system according to claim 1, wherein the workspace comprises physical objects subjected to the actions performed by the user during the training exercise.

24. The system according to claim 20, wherein the computing of the simulated 3D dynamic environment comprises replicating the physical objects in the simulated 3D dynamic environment.

25. A computer-implemented method for training and qualification of a user performing a skill-related training exercise involving body motion in a workspace, comprising performing with a computer:
selecting with the computer a training environment related to the training exercise to be performed from a training database;
adjusting with the computer variables, parameters and controls of the training environment and training exercise;
monitoring with the computer use of an input device providing the user with a physical feeling of an object normally used to perform the training on a real or virtual assembly, wherein the input device is a real or dummy welding torch;
measuring 3D angles and spatial coordinates of reference points relative to the input device and an organ of vision of the user during performance of the training exercise, wherein measuring is performed with at least two sensors having conical fields of view, at least one sensor configured to measure the 3D angles and spatial coordinates of reference points relative to the input device and at least one sensor configured to measure the 3D angles and spatial coordinates of reference points relative the organ of vision of the user;
computing with the computer an organ of vision-object relation as a function of the 3D angles and spatial coordinates;
computing with the computer a simulated 3D dynamic environment in real time as a function of the training environment selected, the simulated 3D dynamic environment reflecting effects caused by actions performed by the user on objects in the simulated 3D dynamic environment as tracked from the input device and the 3D angles and spatial coordinates;
generating with the computer images of the simulated 3D dynamic environment in real time on a display device viewable by the user of the training exercise as a function of the organ of vision-object relation;
recording with the computer data indicative of the actions performed by the user and the effects of the actions; and
setting with the computer user qualification as a function of the recorded data,
wherein setting user qualification comprises comparing the recorded data to a welding standard or code and granting certification if the recorded data meets or exceeds the acceptance criteria of the welding standard or code.

26. The computer-implemented method according to claim 25, wherein the input device comprises a physical object imitating a tool normally used to perform the training exercise, and the simulated 3D dynamic environment comprises a more realistic virtual representation of the tool than the physical object used as the input device.

27. The computer-implemented method according to claim 25, further comprising measuring elapsed time during the training exercise for timing functions of the training exercise.

28. The computer-implemented method according to claim 25, further comprising detecting a collision condition during the training exercise while computing the simulated 3D dynamic environment, and relaying the collision condition to the user.

29. The computer-implemented method according to claim 25, wherein the display device is integrated in one of a pair of goggles, a helmet and a structure wearable by the user during the training exercise to be viewable at all time during performance of the training exercise.

30. The computer-implemented method according to claim 25, further comprising superimposing virtual images over other virtual images in the images on the display device as modeled from the computing of the simulated 3D dynamic environment.

31. The computer-implemented method according to claim 25 wherein the display device has a degree of transparency letting the user see the workspace.

32. The computer-implemented method according to claim 25, further comprising superimposing informative data over the simulated 3D dynamic environment in the images and the display device.

33. The computer-implemented method according to claim 25, further comprising initiating the training exercise by a user action on one of the input device and a computer apparatus implementing the method.

34. The computer-implemented method according to claim 25, wherein the computing of the simulated 3D dynamic environment comprises virtual modeling of phenomena resulting from the effects, and representation of the phenomena in the images generated on the display device.

35. The computer-implemented method according to claim 34, wherein the phenomena comprise changes of states and properties of matter at interfaces and in portions of objects in the simulated 3D dynamic environment.

36. The computer-implemented method according to claim 34, wherein the phenomena comprise possible defects resulting from a poor performance of the user during the training exercise.

37. The computer-implemented method according to claim 25, wherein the computing of the simulated 3D dynamic environment comprises determining essential variables typical to a skill associated with the training exercise.

38. The computer-implemented method according to claim 37, wherein the essential variables comprise trajectory, speed and skill activity angle of objects interacted with during the training exercise.

39. The computer-implemented method according to claim 37, wherein the computing of the simulated 3D dynamic environment comprises linking the 3D angles and spatial coordinates of the reference points to the essential variables.

40. The computer-implemented method according to claim 25, wherein the variables, parameters and controls comprise a tolerance degree for qualification of the training exercise.

41. The computer-implemented method according to claim 25, wherein the user qualification is set by pixel analysis of the data recorded.

42. The computer-implemented method according to claim 25, wherein the workspace comprises physical objects subjected to the actions performed by the user during the training exercise.

43. The computer-implemented method according to claim 25, wherein the computing of the simulated 3D dynamic environment comprises replicating the physical objects in the simulated 3D dynamic environment.

44. The computer-implemented method according to claim 25, further comprising performing a third party certification of a user.

45. The computer-implemented method according to claim 44, wherein certification comprises a database search of law, standards, or law and standards.

* * * * *